US 6,621,263 B2

(12) United States Patent
Al-Janabi et al.

(10) Patent No.: US 6,621,263 B2
(45) Date of Patent: Sep. 16, 2003

(54) HIGH-SPEED CORROSION-RESISTANT ROTATING CYLINDER ELECTRODE SYSTEM

(75) Inventors: Yahya T. Al-Janabi, Qatif (SA); Arnold L. Lewis, II, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 10/002,787

(22) Filed: Oct. 30, 2001

(65) Prior Publication Data
US 2003/0080749 A1 May 1, 2003

(51) Int. Cl.⁷ .............................................. G01N 27/26
(52) U.S. Cl. ...................... 324/200; 324/21.2; 324/444; 324/694
(58) Field of Search ................................ 324/700, 71.1, 324/71.2, 439, 444, 425, 694, 689; 204/212, 280, 400, 403; 73/54.22, 54.28

(56) References Cited

U.S. PATENT DOCUMENTS

| 3,694,338 A | 9/1972 | Weingarten |
| 3,882,011 A | 5/1975 | Hines et al. ............ 204/195 R |
| 4,605,626 A | 8/1986 | Beck .......................... 435/291 |
| RE32,920 E | 5/1989 | Matson et al. ............... 204/1 T |
| 4,882,029 A | 11/1989 | Eickmann .................... 204/400 |
| 4,889,608 A | 12/1989 | Eickmann .................... 204/212 |
| 5,006,786 A | 4/1991 | McKubre et al. ........... 324/71.2 |
| 5,228,976 A | 7/1993 | Abys et al. .................. 204/434 |
| 5,413,692 A | 5/1995 | Abys et al. .................. 204/434 |
| 5,610,325 A | 3/1997 | Rajagopal et al. .......... 73/54.39 |
| 5,770,795 A | 6/1998 | Behar et al. ................ 73/43.23 |
| 5,858,204 A | 1/1999 | Jambo et al. ................ 205/775 |

FOREIGN PATENT DOCUMENTS

DD  298 063  10/1983

OTHER PUBLICATIONS

Pine Instrument Company AFCPRB Electrode Rotator Nov. 1998.
Pine Instrument Company AFMSRX Electrode Rotator Nov. 1998.
Pine Instrument Company AFASR Electrode Rotator Nov. 1998.

Primary Examiner—Jay Patidar
Assistant Examiner—Vincent Q. Nguyen
(74) Attorney, Agent, or Firm—Abelman, Frayne & Schwab

(57) ABSTRACT

A high-speed corrosion-resistant rotating cylinder electrode test apparatus for monitoring of corrosion rates of metals includes an electrochemical/permeation cell body adapted to contain a fluid whose corrosive effect is to be monitored, the cell body having a base at a lower surface thereof and the base having an aperture therethrough. A counter electrode/reference electrode complex is mounted within the cell. The system further includes a cylindrical working electrode and a rotatable system shaft having a lower portion below the base and extending therefrom through the aperture into the cell body, the working electrode being mounted on an upper portion of the system shaft to be positioned within the cell body for rotation. A cone-shaped cap formed from a corrosion-resistant polymeric material is positioned above the working electrode and extends upwardly a relatively short distance into the fluid to reduce vortex phenomena. A motor is connectable to the system shaft for rotating the system shaft. The components of the test apparatus are made of corrosion-resistant materials.

20 Claims, 5 Drawing Sheets

HIGH-SPEED CORROSION-RESISTANT ROTATING CYLINDER ELECTRODE SYSTEM

FIELD OF THE INVENTION

This invention relates to the testing of corrosion of metals in corrosive environments, and in particular to test devices for simulating the conditions encountered in the oil field industry to determine the corrosion rates of metals subjected to such environments.

BACKGROUND OF THE INVENTION

In the oil field industry, drill bits, pipelines and their support structures often face highly corrosive environments including but not limited to hydrogen sulfide environments. Moreover, the drill bit in operation will encounter these corrosive fluids at high rotation speeds. In order to maintain the drilling structures, ex situ tests measuring the corrosive effects of these fluids are performed, advantageously under conditions simulating the aggressive flow regimes usually encountered in the field.

However, conventional lab-based test devices for ex situ monitoring of the corrosive rates of various metals in response to these highly corrosive flowing fluids suffer from several drawbacks. First, conventional lab-based test devices are unable to simulate the aggressive flow regimes sufficiently over the relatively long periods of time necessary for useful test devices, e.g. over a week or more. In particular, the creation of vortex phenomena in the vicinity of the test electrodes disturbs the flow regimes and renders the results inaccurate, since the flow of corrosive fluid past the test electrodes will be unstable. Such vortex phenomena are created, for example, by an asymmetrical shape of the test electrodes, in particular the working electrode of a conventional three electrode structure. However, even in the case of a cylindrical working electrode, such as disclosed in U.S. Pat. No. 5,006,786, insufficient attention has been given to preventing the creation of vortices.

A further limitation of conventional test devices is their inability to handle very corrosive test environments, for example, wet hydrogen sulfide, carbon dioxide, high temperature and test solutions with high salt content. This inability arises from the insufficient corrosion resistance of the materials of the test devices themselves. The result is a significant reduction in the useful lifetime of the test device. A significant limitation of conventional rotating cylinder devices of the prior art is their inability to safely contain hazardous gases such as hydrogen sulfide gas.

Accordingly, it is an object of the present invention to provide a test device for simulating the highly corrosive environments encountered in the oil field industry that overcomes the above-noted limitations of the prior art.

It is a further object of the present invention to provide a test device for simulating the highly corrosive environments encountered in the oil field industry that eliminates or substantially reduces vortex phenomena at the electrode structure, thereby providing a more accurate simulation.

It is a still further object of the present invention to provide a test device for simulating the highly corrosive environments encountered in the oil field industry that has an increased useful lifetime by the use of highly corrosive-resistant materials.

SUMMARY OF THE INVENTION

In accordance with one aspect of the present invention, a high-speed corrosion-resistant rotating cylinder electrode system for ex situ testing and monitoring of corrosion rates of metals comprises an electrochemical/permeation cell body adapted to contain a fluid whose corrosive effect is to be monitored, the cell body having a base at a lower surface thereof and the base having an aperture therethrough. A counter electrode/reference electrode complex is mounted within the cell. The system further comprises a cylindrical working electrode and a rotatable system shaft having a lower portion below the base and extending therefrom through the aperture into the cell body, the working electrode being mounted on an upper portion of the system shaft to be positioned within the cell body for rotation.

In accordance with further especially preferred aspects of the present invention, the system shaft above the cylindrical working electrode has a top in the shape of a cone, and the combination system shaft/working electrode and cone-shaped top projects a relatively short distance up into the cell body. In a further preferred embodiment, the base of the cell body can be depressed below the working electrode. Each of these features of the cylindrical working electrode, the cone-shaped top, the relatively short projection of the system shaft/working electrode and the base depression, serves to completely or substantially eliminate vortex phenomena in the fluid as the system shaft rotates. Any combination these features provides such a significant reduction as to effectively eliminate such phenomena. With the reduction in vortices, the system shaft can be rotated at selected speeds, for example 5,000 rpm, to more effectively simulate the severe flow regimes encountered in the field than was possible with the methods and apparatus known to the prior art.

It is yet a further particularly advantageous aspect of the present invention that the components of the test device are made of corrosion-resistant materials. Specific examples of the advantageous materials for the components of the apparatus are identified below.

Still another aspect of the invention resides in a high-speed corrosion-resistant rotating cylinder electrode combination system for use in monitoring of corrosion rates of metals, said system comprising a plurality of test cells, each test cell including an electrochemical/permeation cell body adapted to contain a fluid whose corrosive effect is to be monitored, the cell body having a base at a lower portion thereof, the base having an aperture therethrough, a counter electrode/reference electrode complex mounted within the cell, a cylindrical working electrode, a rotatable system shaft having a lower portion below the base and extending therefrom through the aperture into the cell body, the working electrode being mounted on an upper portion of the system shaft to thereby be positioned within the cell body for rotation, and a motor connected to the system shaft to cause its rotation; and a base means for mounting the plurality of test cells.

Yet another aspect of the invention resides in a method of operating a high-speed corrosion-resistant rotating cylinder electrode system for the ex situ monitoring of corrosion rates of metals, wherein the system comprises a plurality of test cells, where each test cell comprises an electrochemical/permeation cell body adapted to contain a fluid whose corrosive effect is to be monitored, the cell body having a base at a lower portion thereof and the base having an aperture therethrough, a counter electrode/reference electrode complex mounted within the cell, a cylindrical working electrode, and a rotatable system shaft having a lower portion below the base and extending therefrom through the aperture into the cell body, the working electrode being mounted on an upper portion of the system shaft to be positioned within the cell body for rotation, and a motor connected to the system shaft for rotating the shaft, the system further comprising an overall base for mounting the plurality of test cells, the method comprising the steps of, independently for each test cell, preparing a working electrode formed of a material whose resistivity to a selected corrosive fluid is to be measured, preparing the test cell with the prepared working electrode and the selected fluid, measuring a current flowing between the counter electrode and the working electrode, and calculating a corrosion rate of the sample based upon the measured current.

These and other advantages, aspects and features of the present invention will become apparent upon review of the following detailed description of the preferred embodiments, taken in conjunction with the following drawings.

DETAILED DESCRIPTION OF THE PREFERRED EMBODIMENTS

Before describing embodiments of the high-speed corrosion-resistant rotating cylinder electrode system in accordance with the present invention, a brief description will be given of the underlying theory. Fundamentally, a three electrode system is provided connected to a measuring instrument, such as a conventional potentiostat. The three electrodes are a working electrode, a reference electrode and a counter electrode, all in contact with the fluid under study. The working electrode is formed of the metal of interest, i.e. the metal whose resistivity to the corrosive fluid is being measured. The reference electrode has a fixed electrochemical potential over time, and the counter electrode is made of a corrosion-resistant material and delivers a current to the working electrode. The potentiostat measures the potential of the working electrode with respect to the reference electrode. If this potential is not equal to the desired or "set" potential, the current passing between the counter electrode and the working electrode through the fluid is automatically adjusted so that the measured and set potentials are equal.

Various methods for relating this current and/or the measured potentials to the corrosive effect of the fluid on the metal of the working electrode are well known. One example is found in the above-mentioned U.S. Pat. No. 5,006,786.

Figure 1:
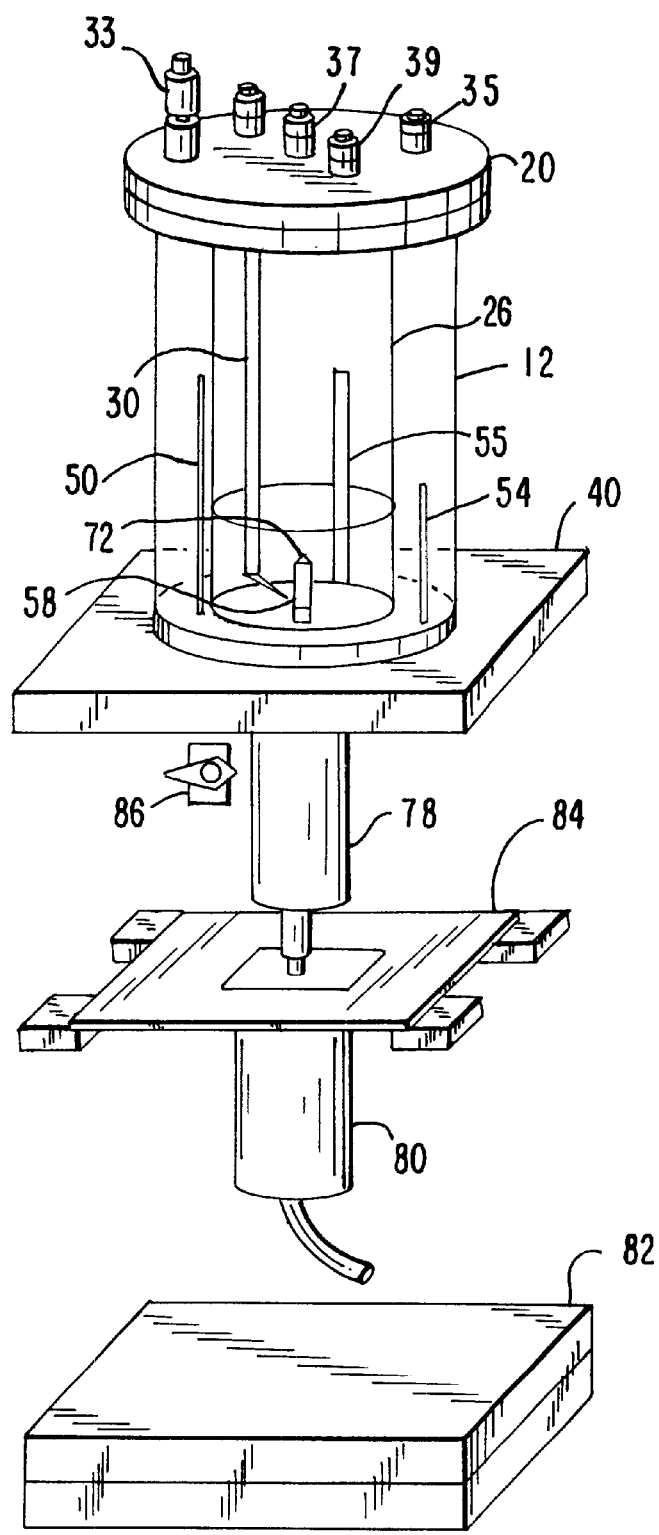
FIG. 1 is a partially exploded view of a simplified first embodiment of a test device incorporating the high-speed corrosion-resistant rotating cylinder electrode system in accordance with the present invention.
Figure 2:
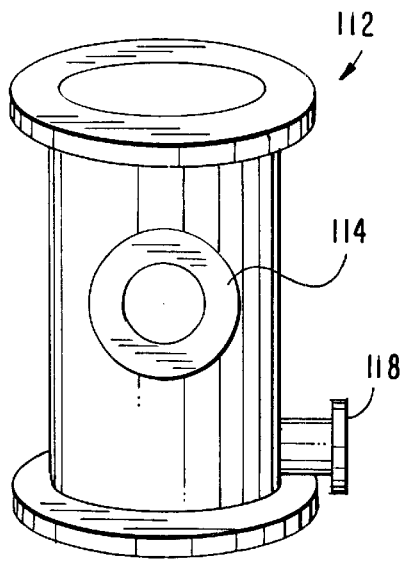
FIG. 2 is front view of a second embodiment of a cell body for use in the test device of FIG. 1.
Figure 3:
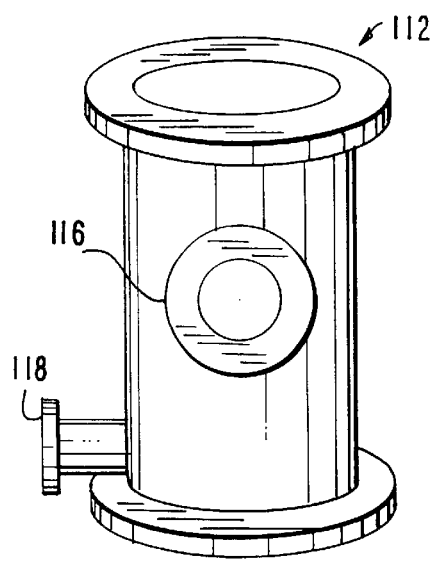
FIG. 3 is a back view of the cell body of FIG. 2.
Figure 4:
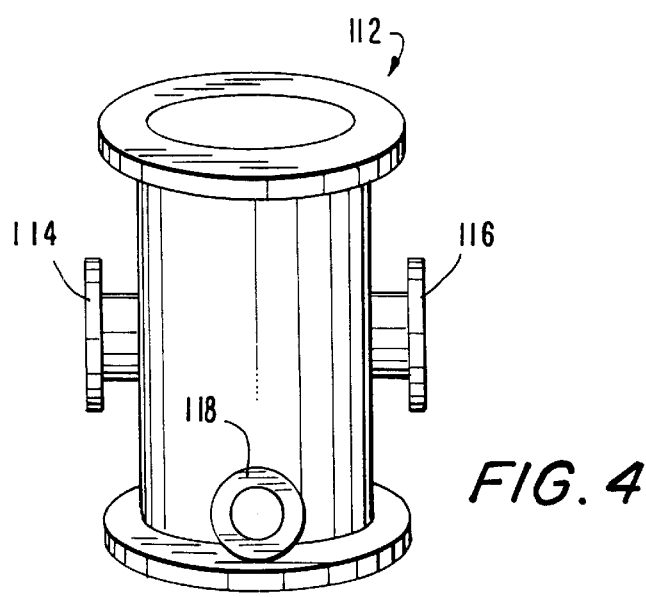
FIG. 4 is a side view of the cell body of FIG. 2.

FIG. 1 is a view of a test device incorporating a first embodiment of the high-speed corrosion-resistant rotating cylinder electrode system in accordance with the present invention. As shown therein, the test device 10 includes a cell body 12 in the form of a heat and chemical resistant glass tube, such as that sold under the Pyrex® trademark. The cell body 12 as illustrated in FIG. 1 is a straight tube suitable for use when only the corrosion rate of the enclosed fluid is being measured. A more complex second embodiment of a cell body is illustrated in FIGS. 2–4 in a more complete form 112, where FIG. 2 is a front view, FIG. 3 is a back view and FIG. 4 is a side view. As shown therein, the complete cell body 112 is a flanged Pyrex® glass tube with two side arms 114, 116 for hydrogen permeation measurements and a smaller third side arm 118 normal to the other two for a scratching apparatus. Such a scratching apparatus simulates sand flow in a pipeline. It will be understood in the following discussion that the cell body in a physical test device could have the structure of the cell body 12, the complete cell body 112, or an intermediate embodiment including only the side arms 114, 116 or the third side arm 118. In these various embodiments, the structure is identical except for the optional presence of the side arms.

Figure 5:
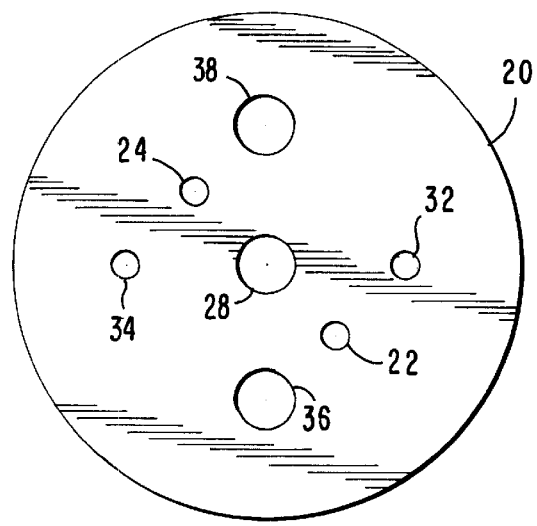
FIG. 5 is a top view of a top of the cell body of FIG. 2.

Returning to FIG. 1, the top 20 of the cell body 12 is made of a corrosion-resistant polymer, such as a polymide-imide. A suitable product is sold by BP Amoco under the trademark Torlon®. As shown in FIG. 5, the top has seven holes and the dotted lines indicate lines of symmetry. Holes 22 and 24 are provided for the fitting of a platinum counter electrode 26 described below, hole 28 for the fitting for a saturated Calomel reference electrode 30 also described below, hole 32 functioning as a gas outlet port for a gas outlet line 33, hole 34 functioning as a chemical injection port 35 and holes 36 and 38 serving as auxiliary or spare ports 37, 39. A first Viton® 0-ring (not shown) resides in a rectangular groove in the top 20 to seal it to the Pyrex® glass of the cell body 12.

Figure 6:
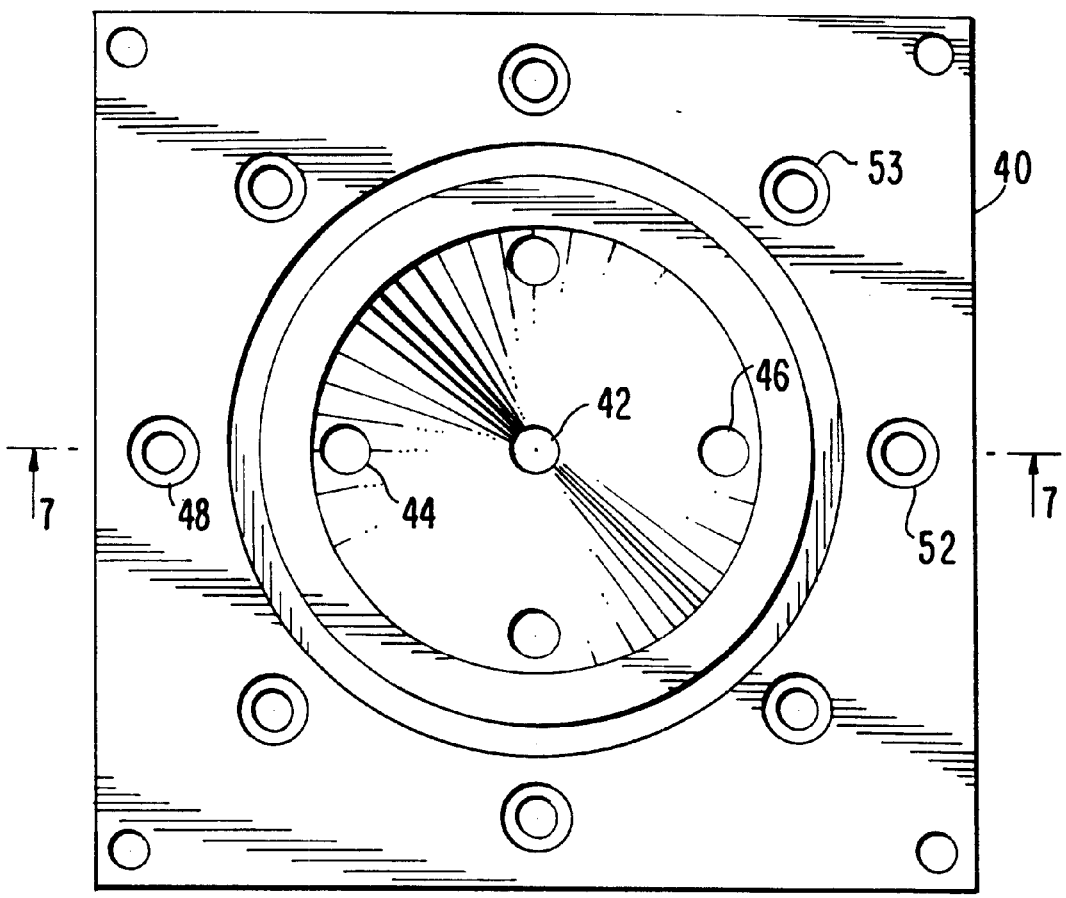
FIG. 6 is a top view of a base of the cell body of FIG. 2.
Figure 7:
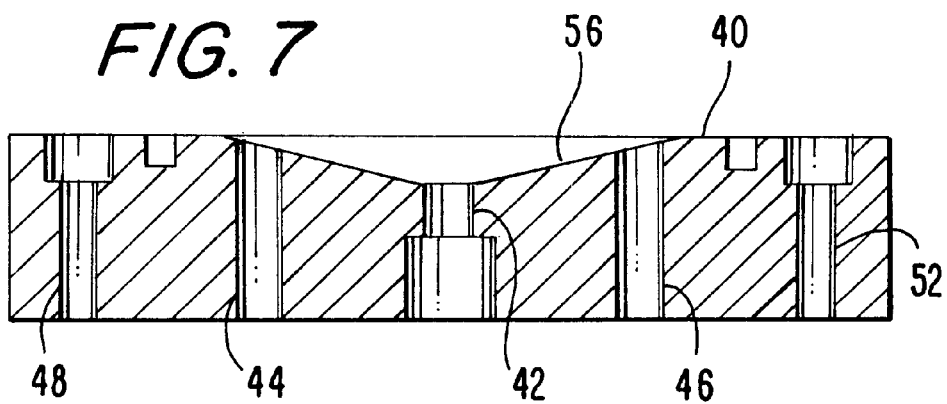
FIG. 7 is a cross-sectional view of the base of FIG. 6, taken along a line A—A in FIG. 6.

The base 40 of the cell body 12 is also made of Torlon®, and includes access holes for access to the interior of the cell body 12, together with other holes for mounting and structural purposes. These holes are shown in FIG. 6, wherein the dotted lines indicate lines of symmetry. As shown in FIG. 6, the access holes include hole 42 for passing the head of a magnetic coupler described below; hole 44 serving as a drainage port, which can also serve as a test/cleaning solution injection port, hole 48 for allowing access therethrough of a heating element 50; hole 52 for a temperature monitoring RTD probe 54; and hole 46 for a gas inlet tube 55. The heating element 50 and the RTD probe 54 are shielded with Inconel, while the gas inlet tube 55 and all of the fittings are made of a corrosion resistant alloy, such as Hastelloy® C-276, available from Haynes International, Inc. of Kokomo, Ind. Eight holes 53 forming a circle are provided for mounting. A second Viton O-ring (not shown) resides in a rectangular groove 59 in the base 40 to seal it to the cell body 12. As shown in FIG. 7, the top surface 56 of the base 40 is depressed slightly in the center portion to minimize artificial disturbances to the fluid flow, minimize turbulence and promote laminar flow conditions. The angle of depression may advantageously be about 7 degrees.

Figure 8:
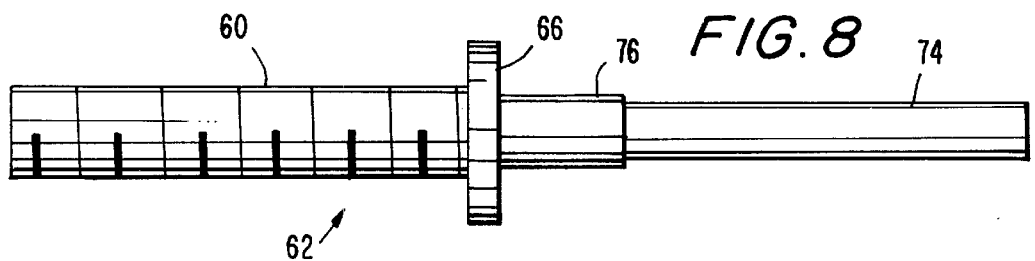
FIG. 8 is a cross-sectional view of the system shaft of the test device of FIG. 1.

The working electrode 58 is a rotating cylinder made of mild steel. It threads into an upper portion 60 of a system shaft 62 as best shown in FIG. 8, and is positioned between top and bottom corrosion resistant polymeric spacers 64, 66 e.g., of Torlon® with Viton® 0-rings (not shown) sealing the gaps between them.

The counter electrode 26, which is made of platinum mesh and connected to the measurement system via two platinum rods, is also in the shape of a cylinder within the cell body 12, so that the counter electrode 26 and the reference electrode 30 form an electrode complex. The test solution, generally a highly corrosive fluid, is contained within the cylinder of the counter electrode 26, with the working electrode 58 extending upwardly into the test solution through the base 40 and the reference electrode 30 extending downwardly into the test solution through the top 20. Thus, all three electrodes are in electrical contact with the test solution, and the test solution carries the current between the working electrode 58 and the counter electrode 26.

Figure 9:
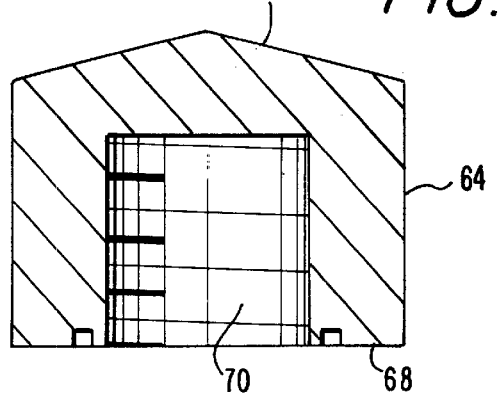
FIG. 9 is a cross-sectional view of a top shaft seal of the system shaft of FIG. 8.

With reference to FIG. 9, the top cap 64 is a cylinder preferably made of Torlon® that is solid or has a closed surface. Its bottom surface 68 contains a threaded aperture 70 that threads onto the upper portion 60 of the system shaft 62. The upper surface 72 of the cap 64 has the shape of a cone to minimize artificial disturbances to the fluid flow at the surface of the working electrode 58. As shown in FIG. 8, bottom spacer 66, also preferably made of Torlon®, is cylindrical and threads onto the system shaft 62.

Advantageously, the length of the working electrode 58 combined with the cap 64 is relatively small compared with the depth of test fluid within the cell body 12. For example, typical dimensions of the working electrode 58 are about 0.625 inch diameter and 0.625 inch length, while the operational depth of the test fluid is typically 6 inches. Moreover, the top of the working electrode is preferably about one inch from the base 40, i.e., the bottom wall of the cell body 12 and approximately five (5) inches of test solution is provided above the top. This configuration assists further in reducing vortex phenomena and therefore helps to yield more accurate test results.

With further reference to FIG. 8, the system shaft 62 is preferably made of Hastelloy® C-276. The system shaft 62 includes the upper portion 60, a lower portion 74 and a middle portion 76. The system shaft 62 is rotated by a magnetic drive 78 positioned below the base 40 of the cell body 12 and engaging an electric motor 80. The magnetic drive 78 includes a magnetic coupler (not shown) having a head that extends through the hole 42 to function as an electrical contact for the rotating cylindrical working electrode 58. The system shaft 62 is directly connected to the magnetic coupler. The magnetic coupler provides both a seal for the rotating system shaft 62 and electrical isolation between the system shaft 62 and the motor 80. The system shaft 62 threads into the magnetic coupler from the top, and the motor 80 is connected to the magnetic coupler from the bottom.

Accordingly, electrical contact to the working electrode 58 is through the system shaft 62 and not, for example, by means of graphite contacts. This structure prolongs the life of the electrical contact, as well as providing more stable electrical contact. This is achieved by using the magnetic couple that electrically isolates the system shaft 62 from the motor 80.

The motor 80 contains a speed control unit and is capable of achieving high rotation speeds, for example 5,000 rpm, that simulate the flow regimes encountered in the field. The cell body 12, the magnetic drive 78 and the motor 80 are supported on an overall base 82 made of stainless steel by four stainless steel legs (not shown including x-y-z positioning components extending from a mount plate 84. Advantageously, the overall base 82 serves as a vibration damper.

A corrosion-resistant pump (not shown) is provided for pumping test and cleaning solutions into the cell body 12 through the drainage/injection port of hole 44 in base 40. The test and cleaning solutions can be removed from the cell body 12 through the drainage/injection port of hole 44 under the control of discharge valve 86.

Figure 10:
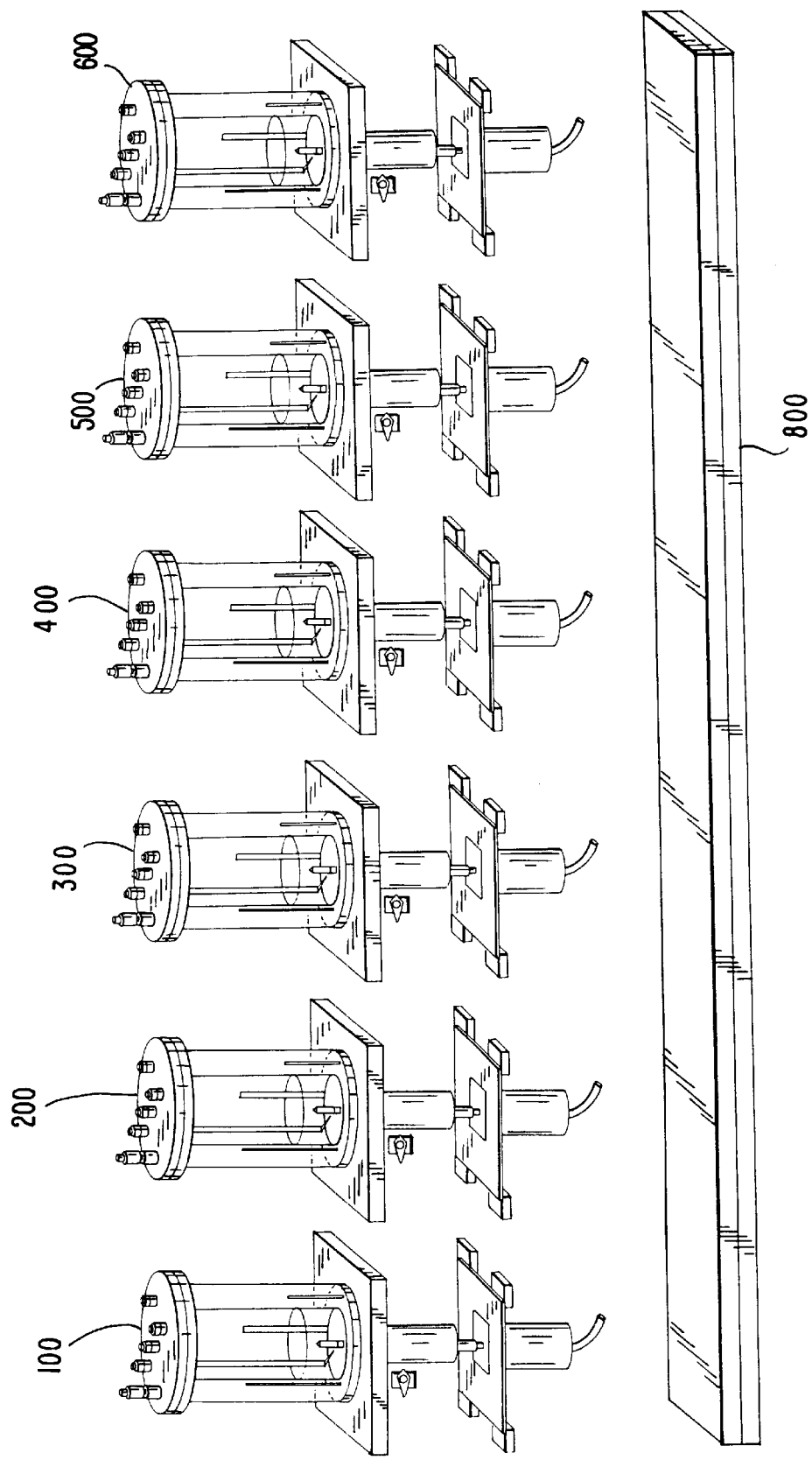
FIG. 10 is a partially exploded view of a simplified second embodiment of a combination of test devices incorporating the high-speed corrosion-resistant rotating cylinder electrode system in accordance with the present invention.

In a further advantageous development as shown in FIG. 10, a base 800 supports the legs for six test devices 100, 200, 300, 400, 500, 600 that are each identical to test device 10 containing any of the above-described cell bodies. These six test devices can be operated simultaneously and independently for rapid evaluations of different test conditions.

The following is a brief description of a method of using the test devices 100–600. First, six fresh test specimen cylinders, i.e. six working electrodes 58, are prepared and installed in the six test devices. The test solutions, which vary according to the particular tests being conducted, are used to fill the test devices, and then the test devices are purged with the required corrosive gases, for example hydrogen sulfide gas. The test devices are then heated, with the temperature being monitored for control. Each test solution is heated by the respective heating probe 50 and the temperature is monitored using the respective platinum resistance temperature device, or RTD, 54.

The rotation speeds of the six test devices are selected and controlled, with each selected rpm being chosen to achieve a required wall shear stress. The corrosion rates of the test cylinders in the six test devices can then be measured using conventional electrical circuitry known in the art for this purpose. The results are multiplexed individually to a single potentiostat, for example an EG&G potentiostat, for the corrosion measurement. As the experiment continues under this control, data is collected using, for example, a personal computer (PC) and mainframe data acquisition and control system for example, a Hewlett-Packard E1421B. Software for this process can be written by one of ordinary skill in the art using well-known methodology and, for example, Microsoft Visual C++ programming tools. Such software advantageously generates six plots of corrosion rate versus time and six plots of temperature versus time, one each for each test device.

Prior to the corrosion measurement procedure, the samples or "coupons" whose corrosion resistance is to be measured are cleaned as follows. First, a glass dish, approximately 25–30 cm in diameter and 15 cm deep, is cleaned with Alkonex® or Tide® detergent. The samples are placed in the clean dish and covered with toluene to 2 cm of liquid. Using gloves, each side of the samples are scrubbed for 30 seconds in the toluene using a new abrasive pad, such as a Scotch Brite® pad, and then the samples are rinsed with acetone, the toluene being discarded. The samples are placed in the dish again and covered with acetone to 2 cm of liquid. Using gloves, each side of the samples are again scrubbed for 30 seconds in the acetone using a fresh abrasive pad; the samples are the rinsed with acetone and placed on a clean absorbent material to dry. The cleaned samples should exhibit no blemishes.

The corrosion measurement method of the invention is now described. A personal computer, or other computing device, switches (i.e. multiplexes) the current test device's working, counter and reference electrodes to the potentiostat's corresponding input, and the potentiostat measures the open circuit potential of the working electrode with respect to the reference electrode. In the first of two measurements, the PC sets the potentiostat's counter electrode potential to the open circuit potential plus 0.01 VDC. The computer then measures the current flowing between the counter and working electrodes through the potentiostat for this first condition.

In the second of the measurements, the PC sets the potentiostat's counter electrode potential to the open circuit potential minus 0.01 VDC. The computer then measures the current flowing between the counter and working electrodes through the potentiostat for this second condition. The computer then calculates the corrosion rate in mils per year of the test cylinder of the current test device using the following formula:

$$MPY = \Delta I \cdot T_a T_b \cdot MW \cdot T \cdot MIL / (\Delta E \cdot \log_e 10 \cdot (T_a T_b) \cdot C \cdot E \cdot D \cdot A \cdot CM)$$

where:

MPY=Corrosion rate in mils (thousandths of an inch) per year, $\Delta I = \text{current}_{(@+0.01\text{-}VDC)} - \text{current}_{(@-0.01\text{-}VDC)}$, in amps, $T_a$=Anodic Tafel constant=0.165

$T_b$=Cathodic Tafel constant=0.165

MW=molecular weight of iron=55.847

T=seconds per year=3.1536E7

MIL=mils per inch=1000

$\Delta E$=0.020 VDC $\log_e 10$=2.303

C=Faraday constant=96487

E=electron charge for corrosion of iron=2

D=density of iron=7.874

A=working electrode area in cm=7.92

CM=centimeters/inch=2.54

These steps can be repeated for different rotation speeds, different temperatures, different test solutions and different gas compositions. If different materials of construction are used for the test cylinders, some of the above constants may differ.

While the above-described embodiment uses all six test devices 100–600 simultaneously, the method of the invention can be practiced using one or any number of the test devices at any one time.

Thus, the test device 10 or combination of test devices 100–600 are designed for unattended continuous operation where parameter settings, for example, rotational speed and solution temperature, are fully automated, e.g., they are controlled and monitored by a computer. As a result, electrochemical corrosion measurements can be conducted ex situ and on a continuous basis.

Moreover, in a further development of the present invention, the test devices 10 and 100–600 can be used to determine atomic hydrogen permeation rates simultaneously with the measurement of corrosion rates. Such hydrogen permeation rate measurements may be made by access through the side arms 114, 116. This unique potential offers significant advantages over conventional test devices.

The benefits derived from the above-described embodiments of the present invention are many and important. The system of the invention provides stable and variable high rotation speeds of the rotating cylindrical working electrode, allowing a better simulation of the aggressive flow regimes typically encountered in the oil industry. The relatively short system shaft/working electrode projection installed from the bottom of the electrochemical testing cell body is designed to prevent vortex phenomena from disturbing flow regimes in the vicinity of the rotating cylindrical working electrode. The cone-shaped top of the working electrode and the depression of the base also assist in reducing the vortex phenomena and simulating field conditions. Thus, the present invention is highly useful in determining the effectiveness of chemical corrosion inhibition programs in, for example, wet-hydrogen sulfide containing environments under simulated fluid flow conditions.

While the present invention has been described with reference to the foregoing embodiments, changes and variations can be made therein which fall within the scope of the appended claims. All such modifications and/or changes are intended to be within the scope of the claims.

What is claimed is:

1. A high-speed corrosion-resistant rotating cylinder electrode system for ex situ monitoring of corrosion rates of metals, comprising:

an electrochemical/permeation cell body adapted to contain a fluid whose corrosive effect is to be monitored, said cell body having a base at a lower surface thereof and said base having an aperture therethrough;

a counter electrode mounted within said cell for introducing an electrical current into the fluid;

a reference electrode mounted within said cell and having a fixed potential overtime;

a cylindrical working elect ode adapted to be connected to a device for measuring a potential of said working electrode over time; and a rotatable system shaft, connectable to a motor for rotation, having a lower portion below said base and extending therefrom through said aperture into said cell body, said working electrode being mounted n an upper portion of said system shaft to be positioned within said cell body for rotation.

2. The system of claim 1, further comprising a motor connected to said system shaft for rotating said shaft.

3. The system of claim 2, further comprising a magnetic drive, wherein said motor is connected to said system shaft through said magnetic drive.

4. The system of claim 1, wherein said working electrode has a corrosion resistant polymeric top in the shape of a cone whereby the formation of a vortex is substantially eliminated during rotation of the electrode in a fluid.

5. The system of claim 4, wherein said working electrode projects upwardly from said base a relatively short distance compared to an operating depth of the fluid in said cell body.

6. The system of claim 1, wherein said working electrode projects upwardly from said base a relativiely short distance compared to an operating depth of the fluid in said cell body.

7. The system of claim 1, wherein a top surface of said base is depressed at a position below said working electrode.

8. The system of claim 7, wherein said working electrode has a corrosion resistant polymeric top in the shape of a cone whereby the formation of a vortex is substantially eliminated during rotation of the electrode in a fluid.

9. The system of claim 8, wherein said working electrode projects upwardly from said base a relatively short distance compared to an operating depth of the fluid in said cell body.

10. The system of claim 1, wherein components of said cell body and said base are formed of highly corrosion-resistant materials.

11. The system of claim 1, wherein said cell body includes a side aperture structure permitting access to the interior of said cell body for testing.

12. A high-speed corrosion-resistant rotating cylinder electrode combination system for ex situ conitoring of corrosion rates of metals, comprising:

a plurality of test cells, each said test cell including:

an electrochemical/permeation cell body adapted to contain a fluid whose corrosive effect is to be monitored, said cell body having a base at a lower surface thereof and said base having an aperture therethrough, a counter electrode mounted within said cell for introducing an electrical current into the fluid, a reference electrode mounted within said cell and having a fixed potential over time, a cylindrical working electrode adapted to be connected to a device for measuring a potential of said working electrode over time, a rotatable system shaft having a lower portion below said base and extending therefrom through said aperture into said cell body, said working electrode being mounted on an upper portion of said system shaft to be positioned within said cell body for rotation, and a motor connected to said system shaft for rotating said shaft; and an overall base for mounting said plurality of test cells.

13. The system of claim 12, wherein each said working electrode has a corrosion resistant polymeric top in the shape of a cone whereby the formation of a vortex is substantially eliminated during rotation of the electrode in a fluid.

14. The system of claim 12, wherein each said working electrode projects upwardly from its respective base a relatively short distance compared to an operating depth of the fluid in the respective cell body.

15. The system of claim 12, wherein a top surface of each said base includes a depressed area at a position below the respective working electrode.

16. The system of claim 12, each said test cell further comprising a magnetic drive, wherein each of the respective motors is connected to its respective system shaft through a respective magnetic drive.

17. A method of operating a high-speed corrosion-resistant rotating cylinder electrode combination system for ex situ monitoring of corrosion rates of metals, wherein the system comprises a plurality of test cells, and each test cell comprises an electrochemical/permeation cell body adapted to contain a fluid whose corrosive effect is to be monitored, the cell body having a base at a lower surface thereof and the base having an aperture therethrough, a counter electrode mounted within said cell for introducing an electrical current into the fluid, a reference electrode mounted within the cell and having a fixed potential over time, a cylindrical working electrode adapted to be connected to a device for measuring a potential of said working electrode over time, and a rotatable system shaft having a lower potion below the base and extending therefrom through the aperture into the cell body, the working electrode being mounted on an upper portion of the system shaft to be positioned within the cell body for rotation, and a motor connected to said system shaft for rotating the shift, the system further comprising an overall base for mounting said plurality of test cells, said method comprising the steps of, independently for each test cell:

preparing a working electrode formed of a material whose resistivity to a selected corrosive fluid is to be measure;

preparing the test cell with the prepared working electrode and the selected fluid;

measuring a current flowing between the counter electrode and the working electrode; and calculating a corrosion rate of the sample based upon the measured current.

18. The method of claim 17, further comprising the step of, independently for each test cell, selecting a rotation speed for the system shaft.

19. The method of claim 17, further comprising the step of, independently for each test cell, selecting a temperature at which the current is measured.

20. The method of claim 17, further comprising the steps of, independently for each test cell:

selecting a corrosive gas for purging the test cell; and purging the test cell wit the selected corrosive gas.

* * * * *